United States Patent [19]

Mustacich

[11] Patent Number: 5,782,964
[45] Date of Patent: Jul. 21, 1998

[54] GAS CHROMATOGRAPHY COLUMN ASSEMBLY TEMPERATURE CONTROL SYSTEM

[75] Inventor: Robert V. Mustacich, Santa Barbara, Calif.

[73] Assignee: RVM Scientific, Inc., Santa Barbara, Calif.

[21] Appl. No.: 790,739

[22] Filed: Jan. 27, 1997

[51] Int. Cl.$^6$ ............................................ B01D 15/08
[52] U.S. Cl. ............................ 96/102; 96/103; 73/23.25; 73/23.27
[58] Field of Search .................. 73/23.25, 23.26, 73/23.27, 23.35; 95/14, 15, 82, 87; 96/101–108, 105; 210/198.2

[56] References Cited

U.S. PATENT DOCUMENTS

| | | | |
|---|---|---|---|
| 3,063,286 | 11/1962 | Nerheim | 96/105 X |
| 3,159,996 | 12/1964 | Norem | 73/23.39 X |
| 4,484,061 | 11/1984 | Zelinka et al. | 210/198.2 X |
| 4,650,964 | 3/1987 | Vincent | 96/101 X |
| 4,726,822 | 2/1988 | Cates et al. | 210/198.2 X |
| 4,805,441 | 2/1989 | Sides et al. | 95/87 X |
| 5,005,399 | 4/1991 | Holtzclaw et al. | 73/23.39 |
| 5,028,243 | 7/1991 | Rubey | 95/87 |
| 5,135,549 | 8/1992 | Phillips et al. | 95/87 X |
| 5,215,556 | 6/1993 | Hiller et al. | 95/87 |
| 5,242,471 | 9/1993 | Markham et al. | 95/87 |
| 5,551,278 | 9/1996 | Rounbehler et al. | 96/101 X |
| 5,611,846 | 3/1997 | Overton et al. | 95/82 X |

OTHER PUBLICATIONS

Holland, et al., "Handheld GC Instrumentation for Chemical Weapons Convention Treaty Verification Inspections", *Field Screening Methods for Hazardous & Toxic Chemicals*, vol. 1, 1995, pp. 229–235.

Göhler, et al., "Fiber Optic Temperature Sensor Using Sampled Homodyne Detection", *Applied Optics*, vol. 30, 1991, pp. 2938–2940.

Appleyard, et al., "Intrinsic Optical Fiber Temperature Sensor Based on the Differential Absorption Technique", *Review of Scientific Instruments*, vol. 61, 1990, pp. 2650–2654.

Maswadeh, et al., "New Generation of Hand–Held, Compact, Disposable Gas Chromatography Devices", pp. 56–59.

Overton, et al., "A New Portable Micro Gas Chromatograph for Environmental Analysis", pp. 207–212.

Overton, et al., "New Horizons in Gas Chromatography: Field Applications of Microminiaturized Gas Chromatographic Techniques", *Trends in Analytical Chemistry*, vol. 13, No. 7, 1994, pp. 252–257.

*Primary Examiner*—Robert Spitzer
*Attorney, Agent, or Firm*—Morton J. Rosenberg; David I. Klein; Jun Y. Lee

[57] ABSTRACT

A temperature control system (10) is provided for controlling temperature parameters in a gas chromatography column assembly (18). The temperature control system (10) includes an extended length capillary gas chromatography column member (12) which contains chemical samples to be analyzed. A heating wire (14) to heat the capillary gas chromatography column member (18) is mounted adjacent to column member (12) and extends throughout a length of the column member (12) extension. A dielectric temperature sensing mechanism for measuring the temperature of the capillary gas chromatography column member (12) is mounted adjacent the column member (12) and provides for minimizing any possibility of electrical shorting within temperature control system (10).

12 Claims, 5 Drawing Sheets

GAS CHROMATOGRAPHY COLUMN ASSEMBLY TEMPERATURE CONTROL SYSTEM

BACKGROUND OF THE INVENTION

FIELD OF THE INVENTION

The subject invention is directed to gas chromatography systems. In particular, this invention relates to apparatus for temperature measurement and control of gas chromatography column assemblies. Still further, this invention pertains to temperature control systems for controlling temperature parameters in gas chromatography column assemblies which includes the combination of a chromatography column member, a heating mechanism for heating the gas chromatography column member and a temperature sensing mechanism for measuring the temperature of the gas chromatography column member. Still further, this invention relates to a temperature control system where a gas chromatography column member, a heating mechanism and a temperature sensing mechanism are mounted in close proximity each to the other. Additionally, this invention pertains to a temperature control system where a temperature sensing mechanism is formed of a dielectric material composition to minimize any possibility of electrical shorting with respect to a closely placed or located heating mechanism in the form of electrical wire. Still further, this invention relates to a temperature control system where a dielectric temperature sensor is fabricated from materials which are similar to or identical to a capillary gas chromatography column member which provides for the temperature sensor properties to closely match the thermal properties of the gas chromatography column member.

PRIOR ART

Prior art temperature measurement elements for temperature control of gas chromatography columns have typically in the past consisted of metallic compositions which change or vary their electrical resistivity with changing or variations in temperature. Such prior art systems used resistance temperature devices to regulate the temperature of gas chromatography ovens.

Some prior art systems such as those described by Holland, et al. in "Handheld GC Instrumentation for Chemical Weapons Convention Treaty Verification Inspections," Field Screening Methods for Hazardous Wastes and Toxic Chemicals, Vol. 1, Air & Waste Management Association, Pittsburgh, 1995, pp. 229–235, show a heated capillary column assembly for a miniature GC in which a co-axial heater wire and co-axial RTDs are used to control the temperature of the capillary gas chromatography column. However, since the resistance thermal devices (RTDs) are formed of a metallic composition, these examples of integration and miniaturization bring the conductive heating elements and conductive RTD elements in close proximity to each other which may result in electrical shorting between these elements and further the transfer of electrical noise from one element to another. Electrical shorting has in the past been found to cause a failure of the temperature sensing circuitry and has led to runaway heating and destruction of the heated capillary column assembly within prior art instruments. Severe noise pick-up by RTDs has been observed in situations where electrical heaters are regulated through modulation of the electrical current, which is generally referred to as pulse width modulation however this modulation results in significant noise radiation which is picked-up by co-axial RTD elements and then propagates in the electrical circuits which disadvantageously affects the computerized control circuits.

In other prior art such as that shown in U.S. Pat. No. 4,726,822, the capillary column is combined with the heating element by using a metallic thin film layer of metal to resistively heat the capillary column instead of using a separate co-axial heater wire. This prior art type of assembly does not use the temperature sensor and the combination of this assembly with an RTD would provide a miniature assembly capable of temperature control however such would be susceptible to electrical shorting and noise interference, as previously discussed.

The above-referenced problems have been found to be of a serious nature when the temperature sensing and heating elements are located in close proximity to each other over an extended distance. It has generally been the objective to use a single temperature sensor such as an RTD to make a distributed measurement of temperature along the length of the column to determine an average or integrated temperature. Increasing the extent of these adjacently located elements has been found to substantially increase the noise pick-up by the sensor circuitry. Films of insulation may be used on these elements however, this limits the operable temperature range and can affect the thermal conduction properties of the elements which will then have an overall effect of increasing power consumption by increasing the thermal mass of the heated components. Some type of thin film insulations may be used on the elements however, such have only been found in the prior art to be partially effective in preventing electrical shorting between the adjacently located elements.

SUMMARY OF THE INVENTION

This invention provides for a temperature control system for controlling temperature parameters in a gas chromatography column assembly which includes an extended length capillary gas chromatography column member having or containing a chemical sample to be analyzed. A heating mechanism to heat the capillary gas chromatography column member extends substantially throughout the length of the capillary gas chromatography column member and is mounted or located adjacent thereto. A temperature sensing mechanism for measuring the temperature of the capillary gas chromatography column member is formed of a dielectric material composition and extends throughout at least a portion of the extended length of the capillary gas chromatography column member.

An object of the subject invention is to provide an electrically non-conducting, dielectric temperature sensing element which provides temperature measurement in close proximity to a heating element for temperature control of a predetermined length of a capillary gas chromatography column.

It is a further object of the invention to provide a temperature sensor within the gas chromatography column assembly which is formed of a dielectric material composition which will not short-circuit when placed adjacent to, contiguous with, or in otherwise close proximity to an electrical heating element and further will not pick up any electrical noise from current modulated heating elements. Such a sensing element can be used by a heater control circuit without electrical interference from noise pick-up by the sensor or electronic circuit failure resulting from electrical shorting with other electrical elements such as a resistively heated wire.

A still further object of the invention is to provide a single dielectric temperature sensing element that can perform a distributed temperature measurement along a predetermined length of a coaxial heating element. This object allows for close proximity or contiguous mounting of the dielectric sensing element with the heating element for integration and miniaturization of temperature sensing and heating elements with a capillary gas chromatography column assembly which is important in reducing the size and power consumption of heated gas chromatography column assemblies as well as insuring freedom from electrical shorting and noise interference in the electronic control circuits.

It is a still further objective of the invention to provide a temperature sensing element having a similar composition to the capillary gas chromatography column member which allows a close or precise match between the thermal mass and thermal conduction properties of the temperature sensor and the capillary gas chromatography column member by the choice of dielectric temperature sensor materials to insure that the temperature measured by the sensing element is representative of the temperature in the capillary gas chromatography column member.

A still further object of the subject invention is the use of a dielectric temperature sensor as a control element providing a small thermal mass and low thermal conductivity which are found with many dielectric sensing elements compared to metallic sensing elements to allow reduction of the power consumption.

DESCRIPTION OF THE PREFERRED EMBODIMENTS

Figure 1:
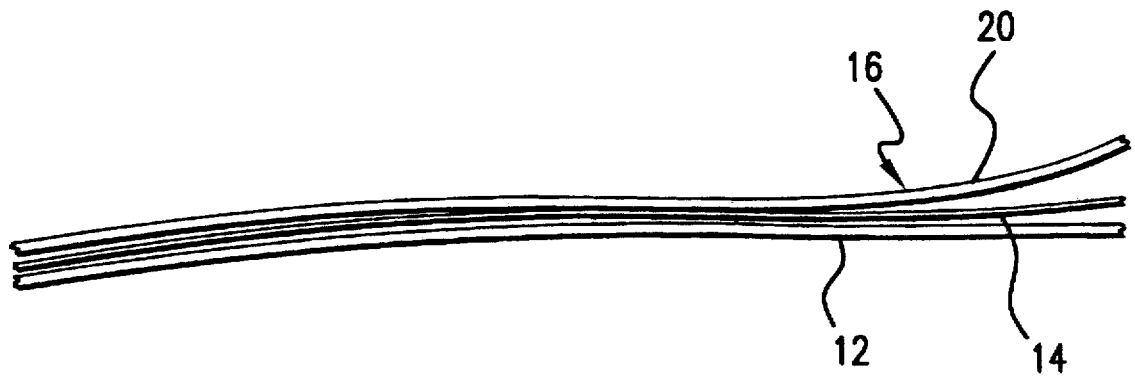
FIG. 1 is a schematic view of a dielectric temperature sensing mechanism in combination with a capillary gas chromatography column member and a heating mechanism mounted in close proximity each to the other.

Referring now to FIGS. 1–5, there is shown temperature control system 10 for controlling temperature parameters in a gas chromatography column assembly. Although not limited thereto, temperature control system 10 is particularly adaptable to miniature capillary gas chromatography column assemblies which requires particular packing considerations as well as unique positional location of the elements forming system 10 to provide a low volume and low weight overall gas chromatography column assembly. Temperature control system 10 as herein described provides for electrical insulation between the elements and minimizes the possibility of any electrical shorting between the aforementioned elements forming system 10. By use of the subject temperature control system 10, close proximity and/or contact of temperature sensor 16 with respect to heating mechanism 14 is provided to allow miniaturization and further the reduction of power consumption. Additionally, by use of system 10, such is substantially immune to any direct electrical noise pick-up from heating mechanism 14. By matching materials either 14 similar to or identical to capillary gas chromatography column member 12 with respect to the fabrication of temperature sensor 16, the overall capillary gas chromatography column assembly may be miniaturized where the properties of the temperature sensor 16 closely match the thermal properties of the capillary gas chromatography column member 12.

Figure 2:
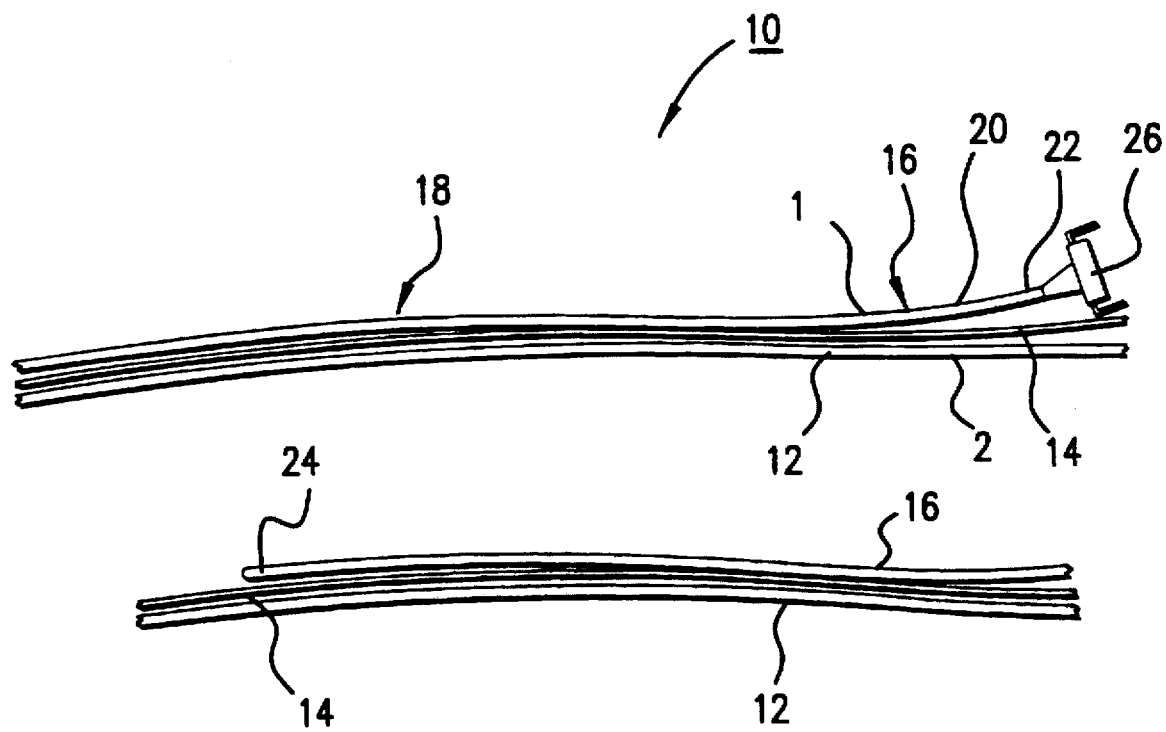
FIG. 2 is a schematic view of the temperature control system 10 of the subject invention showing the ends of the dielectric temperature sensor fabricated from a capillary column and a pressure transducer.

Referring now to FIG. 1, there is shown the basic elements making up temperature control system 10 provided in FIG. 2. As is seen, extended length capillary gas chromatography column member 12 is provided which contains a chemical sample to be analyzed. Capillary gas chromatography column member 12 may be formed typically of a fused silica capillary column and may consist of dielectric materials such as fused silica and polymeric interior as well as exterior coatings. Such dielectric gas chromatography column members 12 are well-known in the art and commercially available.

Temperature control system 10 further includes heating mechanism 14 for heating capillary gas chromatography column member 12 to a predetermined temperature. Heating member 14 as can be seen in FIGS. 1 and 2 extends substantially throughout the extended length of capillary gas chromatography column member 12 and is located adjacent or in contiguous contact therewith. It is to be understood that heating mechanism 14 may be formed of a standard resistively heated electrical element in the form of an electrical wire member. Heating mechanism or heating member 14 is used to control the temperature of capillary gas chromatography column member 12. It is to be understood that although shown in the schematic drawings of FIGS. 1 and 2 as a heating wire member extending adjacent column member 12, heating member 14 may be helically coiled around column member 12 or otherwise positioned to provide appropriate heat transport to capillary gas chromatography column member 12 and the chemical sample contained therein.

It is to be further understood that the capillary gas chromatography column assembly 18, formed of column member 12, heating mechanism 14, and temperature sensor mechanism 16 may be formed into a coiled relation or in an overlying relation to provide a densely packed set of elements which is capable to be inserted within insulated enclosures so that overall lengths ranging from 1 meter to 30 meters or more may be combined within a small volume such as an oven and held to a controlled and programmed temperature. In overall concept, temperature control system 10 provides for the combination of elements which allows a temperature sensor mechanism 16 to provide an integrated and average measurement of the capillary gas chromatography column member 12 temperature.

Temperature control system 10 further includes temperature sensing mechanism 16 for measuring and sensing the temperature of capillary gas chromatography column member 12. Temperature sensing mechanism 16 as can be seen in FIGS. 1 and 2 extends throughout a significant or at least a portion of the extended length of capillary gas chromatography column member 12 and is also mounted adjacent thereto as was described for heating member 14. An important concept of the subject invention control system 10 is that temperature sensing mechanism 16 is formed of a substantially dielectric material composition. Temperature sensing mechanism 16 as herein described provides an integrated average temperature of capillary gas chromatography column member 12 throughout at least the portion of the extended length of capillary gas chromatography column member 12 in the region where temperature sensor mechanism 16 is mounted adjacent column member 12. Temperature sensing mechanism 16 is formed of a material composition having substantially the same thermal mass as capillary gas chromatography column member 12 and is matched to the thermal conductivity of column member 12. Additionally, temperature sensing mechanism 16 is further formed of a material composition having substantially the same thermal conductivity as column member 12 in order to closely match the thermal properties of column member 12 to temperature sensor mechanism 16 as closely as possible.

Temperature sensing mechanism 16 may be a temperature sensing tubular member 20 in the form of a capillary tubular member mounted adjacent capillary gas chromatography column member 12, as is shown in FIGS. 1 and 2. Tubular member 20 is formed of a dielectric material composition and in particular, where gas chromatography column member 12 is formed of a fused silica composition, tubular member 20 may also be formed of substantially the same basic fused silica composition. In the embodiment shown in FIG. 2, temperature sensing tubular member 20 includes first end 22 and second end 24 with the second end being sealed or closed.

As is seen in FIG. 2, first end of tubular member 22 is operatively coupled to pressure transducer 26 which is commercially available and generally has a small internal volume. A pressure transducer 26 of the type used in the subject system is commercially available from SenSym, Inc. having a place of business in Milpitas, Calif. and a Model Number SDX05G2. In this embodiment, tubular member 22 is essentially a capillary tubing where second end 24 of tubular member 20 is either fused, glued, or otherwise closed to seal the internal volume of tubular member 20. In this manner, changes in temperature directly results in a linear change in the pressure within tubular member 20 and is read out by the pressure sensor's circuitry (not shown and not part of the invention concept as herein described) as a linear change in the voltage.

Figure 6:
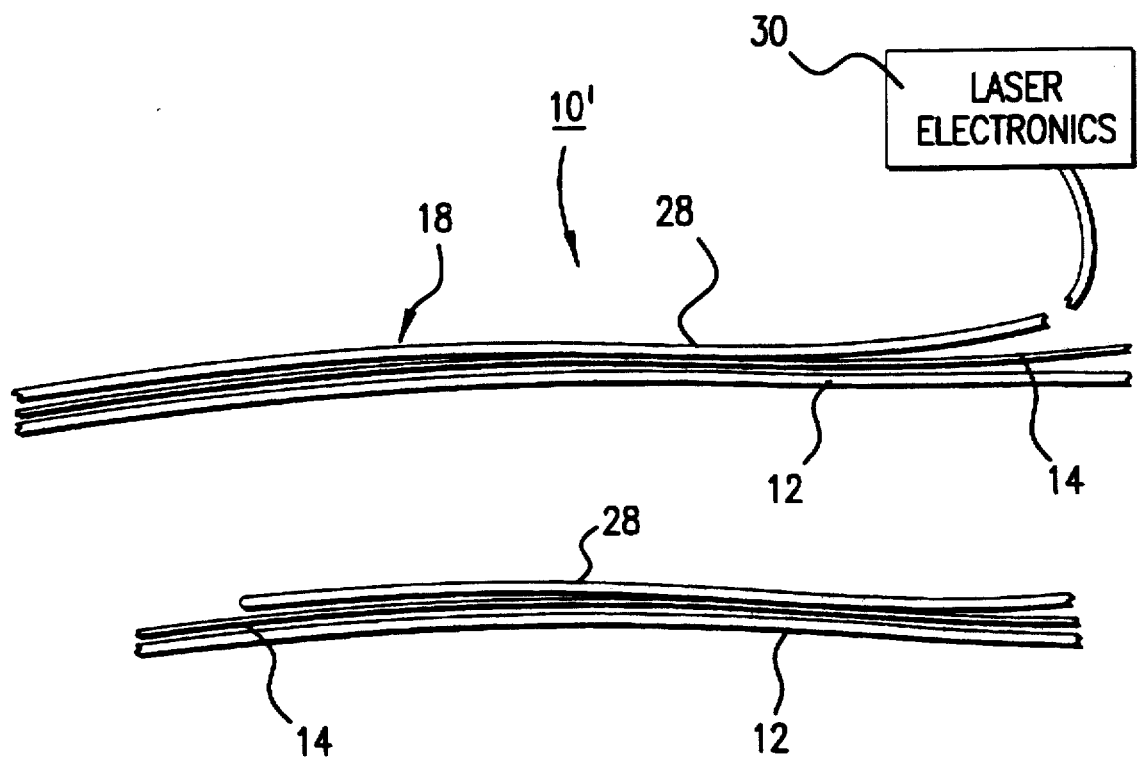

FIG. 6 is directed to an embodiment of temperature control system 10 which utilizes fiber optic element 28 in combination with laser electronics 30. Laser electronics 30 are commercially available and not part of the subject invention concept as herein described. The important concept being that fiber optic element 28 is provided in close proximity and positionally located adjacent capillary gas chromatography column member 12 and heating member 14 as previously described for temperature control system 10. In general, laser electronics 30 would include an interferometer, a laser driver and processing electronics as well as the laser itself. Numerous sensor systems have been used based upon interferometry, and demodulation schemes have been used using heterodyne, homodyne detection. Sensors have been used consisting of a fiber Mach-Zehnder interferometer, laser driver, and processing electronics where the sensor is based on fringe counting in an interferometer with a path difference approximating a few centimeters. Such methods are used to measure thermally induced phase changes produced in wound fiber. Such lasers may be frequency modulated through changes in the injection current, as is well-known in the art. The modulation light may be coupled into the fiber interferometer with the output signal from the interferometer being a combination of the phase change responsive to the laser modulation and the thermally induced phase change in the fiber itself. This type of fiber-optic based dielectric temperature sensor may be integrated coaxially or adjacently located with capillary gas chromatography column member 12 to provide an electrically non-conducting, low thermal mass temperature sensor for heating control of the capillary column assembly 18 as shown.

In particular, and in accordance with the invention concept herein described, a temperature control system 10 was fabricated from a 3.0 meter length fused silica capillary gas chromatography column member 12 through attachment of one end of the tubing to an orifice of a pressure sensor or pressure transducer 26 which was of the type previously discussed as Model Number SDX05G2 manufactured by SenSym, Inc. Second end 24 of tubular member 22 was fused to seal the internal volume of the capillary tubing or tubular member 20 and pressure transducer 26. A change in the temperature within tubular member 20 resulted in a linear change in the pressure which was directly read out by the circuitry of the pressure sensor 26 as a linear change in the voltage.

In using the Model Number SDX05G2 pressure transducer 26 a 0–5 psi pressure change resulted linearly in an amplified voltage change of 0–10 volts. This provided a large output signal change compared to small temperature coefficients of resistance thermal devices (RTD) and allowed for improved accuracy in the electronic temperature control circuits.

Figure 3:
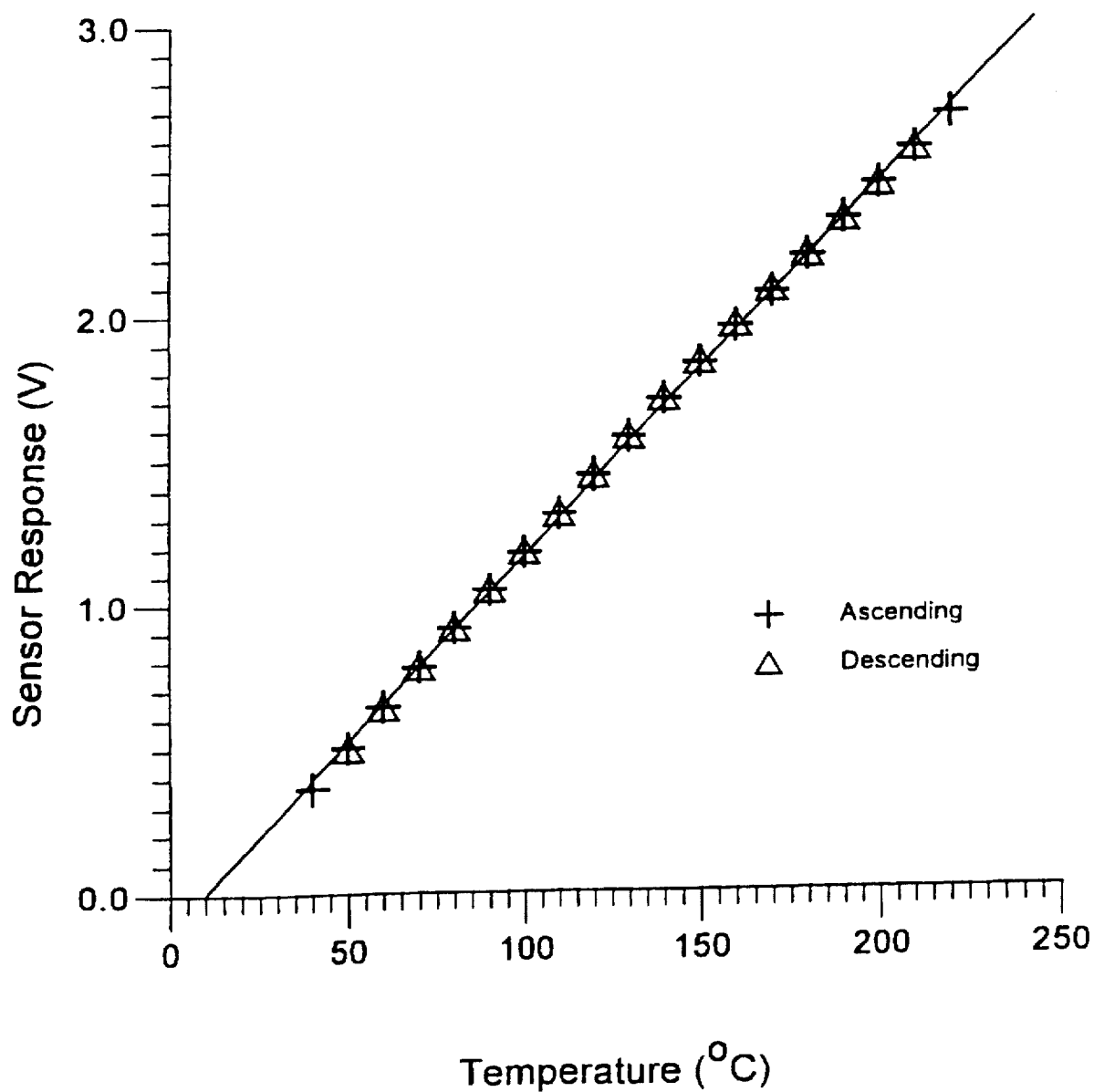
FIG. 3 is a graph showing the amplified response to ascending and descending temperatures of the sensor as provided in FIG. 2.

In the tests run with the SDX05G2 pressure transducer 26 and the aforementioned column member 12 and tubular member 22, linearity and large voltage response was seen, as is shown in FIG. 3. The temperature excursion of approximate ambient temperatures to temperatures in excess of 200° C. is an important range for gas chromatography temperature programming. The FIG. 3 shows excellent linearity of pressure transducer 26. The linearity is achieved as long as the unheated gas volume within the pressure sensor and a small amount of capillary tubing connecting the sensor to the heated region of the capillary tube is relatively small with respect to the total volume within the sensor.

Figure 4:
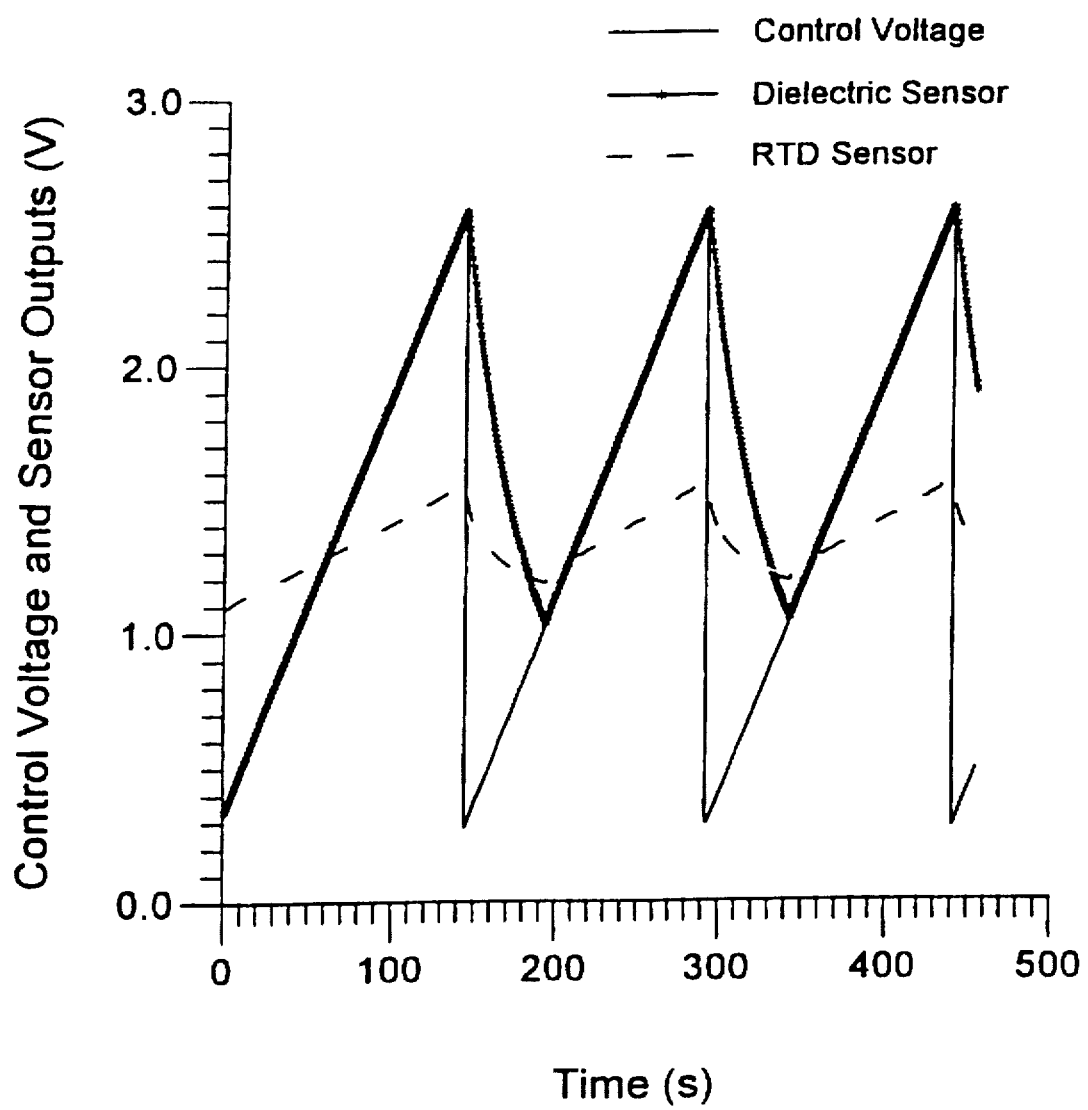
FIG. 4 is a graph showing data from the application of the sensor shown in FIG. 2 to control the pulse-width modulated heating of a capillary gas chromatography column assembly following a computer-generated temperature program.

Tests were run to control temperature in a capillary gas chromatography column assembly 18 which are shown in FIG. 4. The large sawtooth waveform of FIG. 4 is a computer generated control voltage which was programmed to ramp linearly from approximately 0.3 volts to 2.5 volts. The dielectric temperature sensor's output was used in a control circuit to control the electrical current of heater wire 14 in capillary gas chromatography column assembly 18. In this circuit, the dielectric temperature sensor's output was compared with the computer-generated sawtooth waveform as differential inputs to an operational amplifier controlling the gating of current to the heater. Overall this controls the flow of current to the heater so that the temperature rise of the capillary gas chromatography column assembly 18 results in a matching of the dielectric temperature sensor's output voltage with the computer generated sawtooth ramp voltage. Close agreement with the dielectric temperature sensor's signal and the control voltage is seen which results in a substantially linear heating rate of approximately 1.2° C./s and is further shown in FIG. 4.

Following the completion of the computer-generated heating ramp, the capillary gas chromatography column assembly 18 convectively cooled in air until the temperature sensor's output match the value of the next computer-generated ramp of control voltage. For comparison purposes, an RTD wire was included in the capillary gas chromatography column assembly 18 to simultaneously monitor the response of the sensor. The RTD wire was formed of a 0.0025 inch diameter Redi Iron 120 wire manufactured by H. P. Reid, Inc. of Neptune, N.J. This had a relatively large temperature coefficient of 4500 parts per million per degrees C and the RTD trace is shown in FIG. 4 confirming the results of the dielectric temperature sensor.

Figure 5:
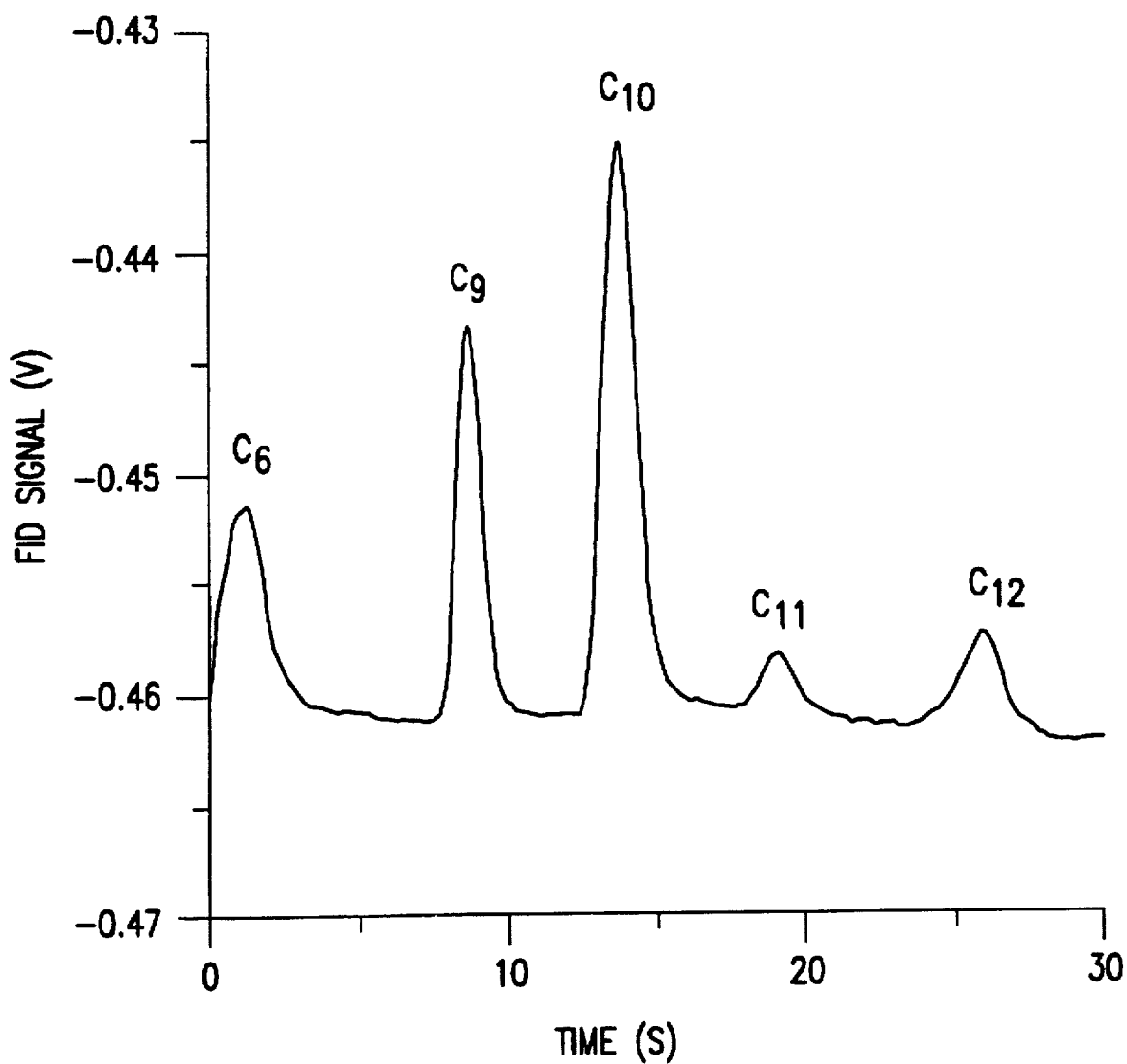
FIG. 5 shows a fast separation of semi-volatile hydrocarbons using a temperature-programmed capillary gas chromatography column assembly using the sensor as shown in FIG. 2; and, FIG. 6 is a schematic drawing of an embodiment of the temperature control system of the subject invention using a fiberoptic element as the temperature sensing mechanism.

Fast temperature program chromatography of capillary gas chromatography column assembly 18 using the subject dielectric temperature sensor is shown in FIG. 5. For this Figure, a capillary gas chromatography column member of approximately 1.0 m.length was used with a flame ionization detector. Helium gas was used as a carrier gas at a flow rate of 10 ml/mm. The gas chromatography column member 12 used in this experiment was a Sulfur-AT column obtained from Alltech Associates, Inc. of Deerfield, Ill. having an inner diameter approximating 0.25 mm. The column 12 and operating conditions provided fast gas chromatography separations having low gas chromatography resolution but sufficient to demonstrate the successive elution of a number of n-alkane hydrocarbons including hexane, nonane, decane, undecane, and dodecane. The hydrocarbons were injected into the 1.0 meter capillary gas chromatography column member 12 which used the dielectric temperature sensor as the temperature controlling sensor. In substantially the same approach as was taken for the tests shown in FIG. 4, heating measured by the dielectric temperature sensor followed a computer-generated control voltage for the temperature programming. The capillary gas chromatography column assembly 18 was initially held at 400° C. during injection and then ramped at a linear temperature programming rate of 2° C./s to a final temperature of 100° C. As is seen in FIG. 5, the heavier hydrocarbons $C_9$–$C_{12}$ eluded rapidly under the influence of the temperature program with approximately equal spacing. In opposition to RTD based miniature co-axial temperature controllers, there was no significant noise due to pulse-width modulation of the current applied to the heating element and obviously there was no failure of any temperature control circuits due to shorting between the temperature sensor and the heater since such is impossible with the use of dielectric temperature sensors.

Although this invention has been described in connection with specific forms and embodiment thereof, it will be appreciated that various modifications other than those discussed above may be resorted to without departing from the spirit or scope of the invention. For example, functionally equivalent element may be substituted for those specifically shown and described, proportional quantities of the elements shown and described may be varied, and in the formation method steps described, particular steps may be reversed or interposed, all without departing from the spirit or scope of the invention as defined in the appended Claims.

What is claimed is:

1. A temperature control system for controlling temperature parameters in a gas chromatography column assembly comprising:

(a) an extended length capillary gas chromatography column member containing a chemical sample to be analyzed;

(b) heating means for heating said capillary gas chromatography column member to a predetermined temperature, said heating means extending substantially throughout said extended length of said capillary gas chromatography column member and located adjacent thereto; and, (c) temperature sensing means for measuring the temperature of said capillary gas chromatography column member, said temperature sensing means extending throughout at least a portion of said extended length of said capillary gas chromatography column member and mounted adjacent thereto, said temperature sensing means being formed of a substantially dielectric material composition.

2. The temperature control system as recited in claim 1 where said temperature sensing means includes means for providing an integrated average temperature of said capillary gas chromatography column member throughout at least said portion of said extended length capillary gas chromatography column member.

3. The temperature control system as recited in claim 1 where said substantially dielectric material composition of said temperature sensing means has a thermal mass that is substantially the same as a thermal mass of said capillary gas chromatography column member.

4. The temperature control system as recited in claim 3 where said substantially dielectric material composition of said temperature sensing means has a thermal conductivity that is substantially the same as a thermal conductivity of said capillary gas chromatography column member.

5. The temperature control system as recited in claim 1 where said temperature sensing means includes:

(a) a temperature sensing tubular member; and, (b) means for measuring pressure within said temperature sensing tubular member.

6. The temperature control system as recited in claim 5 where said temperature sensing tubular member includes a first closed end and an opposing open second end coupled to said means for measuring pressure.

7. The temperature control system as recited in claim 5 where said means for measuring pressure is a pressure transducer.

8. The temperature control system as recited in claim 7 where said temperature sensing tubular member is formed of a fused silica composition.

9. The temperature control system as recited in claim 7 where a change in temperature sensed is linearly converted to a linear change in voltage output by said pressure transducer.

10. The temperature control system as recited in claim 1 where said capillary gas chromatography column member is formed of a fused silica composition.

11. The temperature control system as recited in claim 1 where said heating means is a resistively heated wire member.

12. The temperature control system as recited in claim 1 where said temperature sensing means includes an optical fiber member whereby transmission of light is modulated responsive to a temperature change within said capillary gas chromatography column member.

* * * * *